US011690934B2

United States Patent
Kao et al.

(10) Patent No.: US 11,690,934 B2
(45) Date of Patent: Jul. 4, 2023

(54) BONE IMPLANT COMPOSITION

(71) Applicant: XELITE BIOMED LTD., New Taipei (TW)

(72) Inventors: Chung-Wei Kao, New Taipei (TW); Yung-He Liang, New Taipei (TW)

(73) Assignee: XELITE BIOMED LTD., New Taipei (TW)

( * ) Notice: Subject to any disclaimer, the term of this patent is extended or adjusted under 35 U.S.C. 154(b) by 0 days.

(21) Appl. No.: 17/507,355

(22) Filed: Oct. 21, 2021

(65) Prior Publication Data
US 2022/0125991 A1  Apr. 28, 2022

(30) Foreign Application Priority Data
Oct. 22, 2020  (TW) .................. 109136618

(51) Int. Cl.
| | |
|---|---|
| *A61L 27/00* | (2006.01) |
| *A61L 27/12* | (2006.01) |
| *A61L 27/10* | (2006.01) |
| *A61L 27/46* | (2006.01) |
| *A61L 27/56* | (2006.01) |

(52) U.S. Cl.
CPC .............. *A61L 27/12* (2013.01); *A61L 27/10* (2013.01); *A61L 27/46* (2013.01); *A61L 27/56* (2013.01); *A61L 2430/02* (2013.01)

(58) Field of Classification Search
CPC ...... A61L 31/06; A61L 27/3604; A61L 27/12; A61L 27/10; A61F 2/28
See application file for complete search history.

(56) References Cited

U.S. PATENT DOCUMENTS

2015/0165092 A1* 6/2015 Kaplan .................. A61L 27/56
424/94.1
2020/0390944 A1* 12/2020 Williams ............... A61B 17/80

FOREIGN PATENT DOCUMENTS

| CN | 1830907 A | 9/2006 |
|---|---|---|
| CN | 101264340 A | 9/2008 |
| TW | I643640 B | 12/2018 |

* cited by examiner

*Primary Examiner* — Jason-Dennis N Stewart
(74) *Attorney, Agent, or Firm* — Muncy, Geissler, Olds & Lowe, P.C.

(57) ABSTRACT

This present invention discloses a bone implant composition which comprises about 50~70% by weight of ceramic particles, wherein the ceramic particles composes tricalcium phosphate and bioactive glass; and about 30~50% by weight of carrier. The carrier provides good ability of operation and shaping, so the bone implant composition can be filled into a human body by various shapes. Because of high ratio of ceramic particles, it can still construct supports even if carrier is degraded within a short time after implanted, which is beneficial for adhesion and growth of new bone cells, and also promotes healing of bone defect.

7 Claims, 4 Drawing Sheets
(4 of 4 Drawing Sheet(s) Filed in Color)

BONE IMPLANT COMPOSITION

BACKGROUND OF THE INVENTION

1. Technical Field

This present invention relates to a medical implant for human body. More particularly, this present invention relates to a bone implant composition.

2. Description of Related Art

Bone graft is a common surgical procedure in the clinical orthopedic surgery. It is majorly for repairing bone defect in various situations such as limb fractures, bone diseases, sequestrectomy and joint replacement or repair. There are three common materials to perform as bone graft: autograft, allograft, and synthetic bone graft. The autograft is the best material for having great properties of osteogenesis, osteoconduction and osteoinduction, but it needs to obtain bones from patient. Although allograft is effective for osteoinduction, it needs to find a donor or a bone having histocompatibility with the patient and it still has risks of inducing inflammatory or rejection response. The synthetic bone graft performs no osteogenesis, but is effective for osteoconduction and osteoinduction, and the source is easy to obtain, and often used in clinic.

Most of synthetic bone grafts are bioactive particles, usually in granular or massive, and the compositions are often phosphate or calcium, major chemical compositions in general bone tissue. When it is applied in surgery, granular or massive synthetic bone graft will be hard to fit into a specific bone defect because of its irregularity. In order for surgeons to operate easily in surgery, clay or putty-type products of the synthetic bone graft can meet this requirement. It can be grabbed, molded and formed by a surgeon according to size and shape of the implanted site, and then filled into the specific bone defect.

However, the commercial synthetic bone graft usually has problems with underperformed biocompatibility and fast degradation which not only lead to insufficient adhesion between the implanted synthetic bone graft and new bone cells but also can't construct supports for growing in the bone defect. It further causes impaired healing of the bone defect.

BRIEF SUMMARY OF THE INVENTION

In light of the above, an objective of the present invention is to provide a bone implant composition having a great biocompatibility and can also construct a steady and supportive structure.

To achieve the objective mentioned above, the present invention provides a bone implant composition which comprises about 50~70% by weight of ceramic particles, wherein the ceramic particles comprising tricalcium phosphate and bioactive glass; and about 30~50% by weight of carrier.

Accordingly, the bone implant composition provided by this present invention has a high ratio of ceramic particles comprising tricalcium phosphate and bioactive glass. The tricalcium phosphate can induce adhesion and growth of new bone cells, and the bioactive glass can induce growth factors and promotes growth of new bone cells. So, it can still construct supports even if carrier was degraded within a short time after implanted, which is beneficial for adhesion and growth of new bone cells, and also promotes healing of bone defect.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The following are embodiments and experiments for detailed illustration of the bone implant composition disclosed in the present invention.

Preparation of Tricalcium Phosphate

Micrometer-sized (μm) tricalcium phosphate particles were mixed with cellulose derivatives solution such as cellulose acetate, nitrocellulose, methyl cellulose, ethyl cellulose for 2 minutes. Then, terpenoids particles such as carotene, camphor, rosin acid, menthol with diameters less than 1.18 millimeter (mm) were added, mixed and stirred for 10 minutes for granulation. After the mixtures were sintered for 18 hours under 1000~1200° C., tricalcium phosphate particles with diameter of 0.2~3.0 millimeter were screened by No. 6 mesh and No. 35 mesh.

Figure 1:
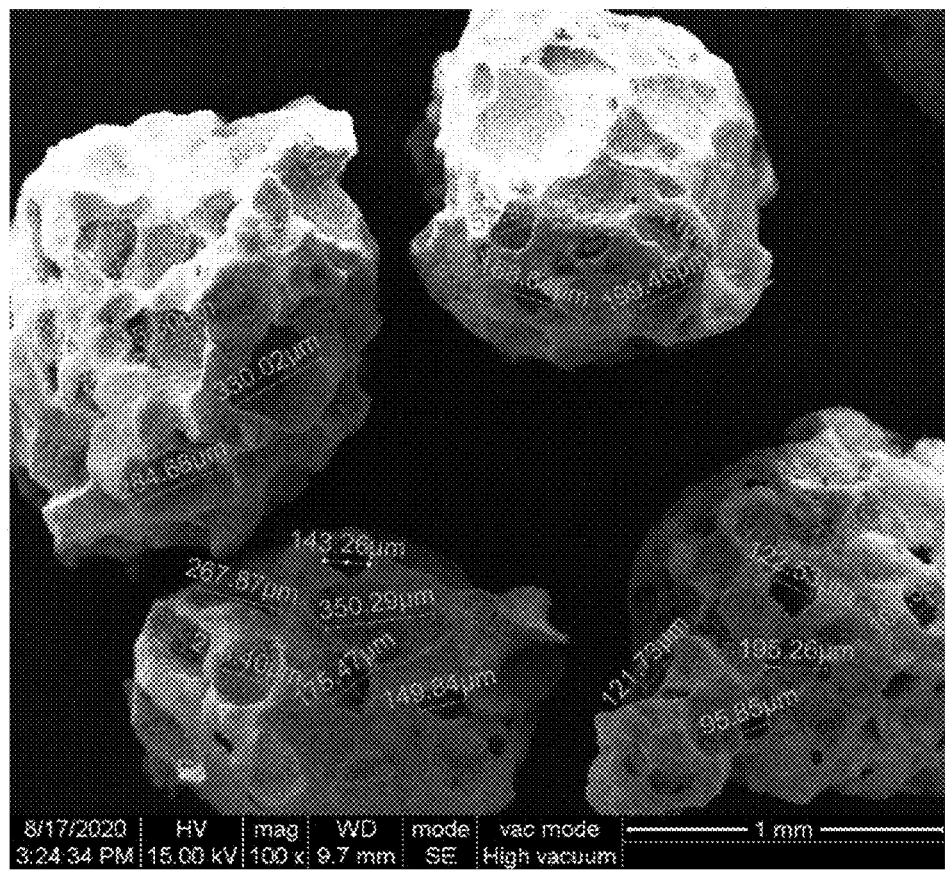
FIG. 1 and FIG. 2 are images of the tricalcium phosphate particles used in the present invention.
Figure 2:
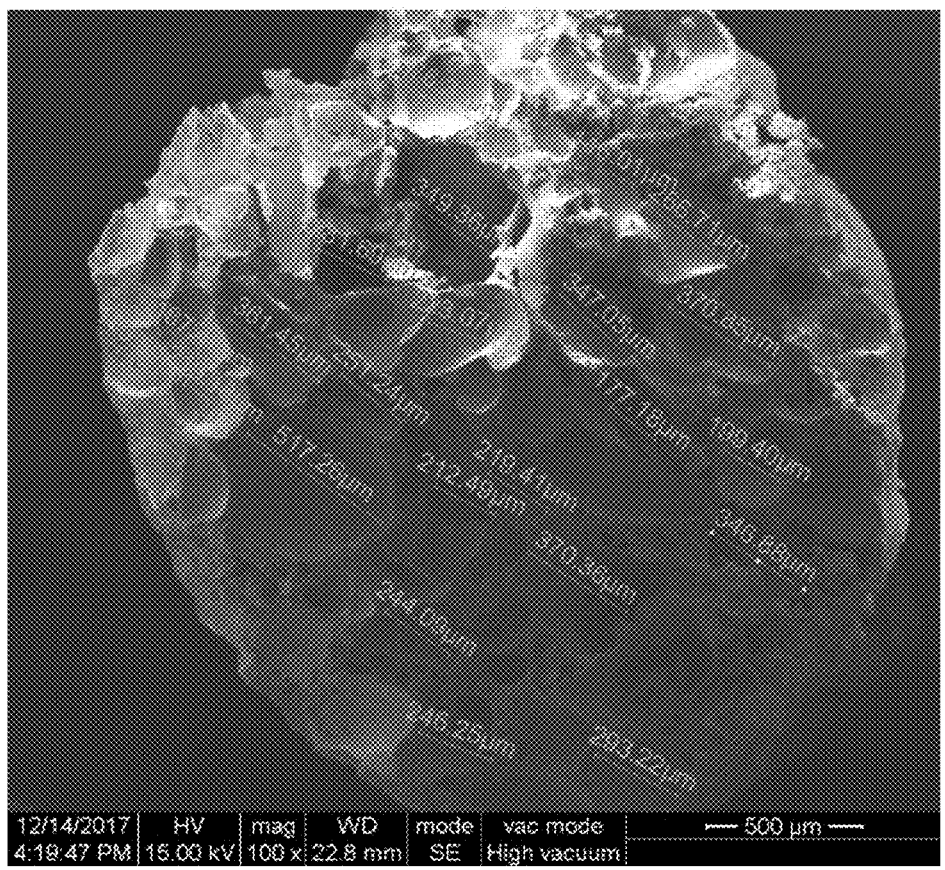

A scanning electron microscope (FEI Inspect S, FEI Company) was used to observe and analyze the tricalcium phosphate particles prepared by above process. As shown in FIG. 1 and FIG. 2, sizes of micro pores on these tricalcium phosphate particles were 100~500 μm.

Three batches of tricalcium phosphate particles were sampled for measurement of porosity by further using a porosimetry (MatsuHaku, GP-120C) through media method with water. The porosity of the tricalcium phosphate particles were 76.74±0.51%, 81.75±1.43% and 82.86±0.36% respectively.

Embodiment 1

All carriers were mixed in 70° C. water bath and then ceramic particles were added. Mixture comprised by weight ratio of 50% ceramic particles and 50% carriers was mixed and stirred for 10 minutes and then cooled to room temperature. Wherein, ceramic particles were comprised by whole weight ratio of 40% tricalcium phosphate and 10% bioactive glass. The weight ratio of tricalcium phosphate and bioactive glass was 1:0.25. The tricalcium phosphate particles were prepared by above process having about 0.2~3 mm diameter and greater than or equal to about 70% porosity. The carrier was comprised by whole weight ratio of 15% glycerol, 25% polyethylene glycol (PEG), 5% carboxymethyl cellulose (CMC) and 5% water.

Revised from the method mentioned in the reference paper "R. Cross, "Elastic and viscous properties of Silly Putty", Am. J. Phys. 80, 870-875 (2012)", a test method was developed to verify the elasticity and viscosity of the final product. A universal materials testing machine (QC-505M2F, Cometech) was used to collect sample data of compressive deformation and compressive force. An upper plate, a lower plate and a load cell were all installed on the universal materials testing machine. A bone implant composition produced by the above process were shaped into a cylindrical specimen (14±2 mm diameter and 30±2 mm height) and then were fixed on the lower plate. After zeroing the load cell, the specimen was compressed for 7 mm with constant speed (15 mm/minute). The data of feedback force and compressive displacement of the specimen during compression were recorded and proceeded into a stress-strain curve. Wherein, stress value equals feedback force divided by compression area, strain equals compressive displacement divided by initial height of specimen and compressive modulus equals slope of the stress-strain curve.

Based on the above test method, compressive modulus of the specimen of this embodiment 1 was 0.29 megapascal (MPa), and it had a soft texture, could be easily shaped, and had excellent handleability during hand test by a controller.

Embodiment 2

All carriers were mixed in 70° C. water bath and then ceramic particles were added. Mixture comprised by weight ratio of 55% ceramic particles and 45% carriers was mixed and stirred for 10 minutes and then cooled to room temperature. Wherein, ceramic particles were comprised by whole weight ratio of 15% tricalcium phosphate and 40% bioactive glass. The weight ratio of tricalcium phosphate and bioactive glass was 1:2.66. The tricalcium phosphate particles were prepared by above process having about 0.2~3 mm diameter and greater than or equal to about 70% porosity. The carrier was comprised by whole weight ratio of 20% glycerol, 23% PEG, 2% CMC and 0% water.

Elasticity and viscosity of the bone implant composition produced by this embodiment 2 was verified through the test method illustrated in the embodiment 1. Compressive modulus of the specimen of this embodiment 2 was 0.11 MPa, and it had a soft texture, could be easily shaped, and had excellent handleability during hand test by a controller.

Embodiment 3

All carriers were mixed in 70° C. water bath and then ceramic particles were added. Mixture comprised by weight ratio of 55% ceramic particles and 45% carriers was mixed and stirred for 10 minutes and then cooled to room temperature. Wherein, ceramic particles were comprised by whole weight ratio of 45% tricalcium phosphate and 10% bioactive glass. The weight ratio of tricalcium phosphate and bioactive glass was 1:0.22. The tricalcium phosphate particles were prepared by above process having about 0.2~3 mm diameter and greater than or equal to about 70% porosity. The carrier was comprised by whole weight ratio of 18% glycerol, 25% PEG, 2% CMC and 0% water.

Elasticity and viscosity of the bone implant composition produced by this embodiment 3 was verified through the test method illustrated in the embodiment 1. Compressive modulus of the specimen of this embodiment 3 was 0.512 MPa, and it had a soft texture, could be easily shaped, and had excellent handleability during hand test by a controller.

Embodiment 4

All carriers were mixed in 70° C. water bath and then ceramic particles were added. Mixture comprised by weight ratio of 65% ceramic particles and 35% carriers was mixed and stirred for 10 minutes and then cooled to room temperature. Wherein, ceramic particles were comprised by whole weight ratio of 25% tricalcium phosphate and 40% bioactive glass. The weight ratio of tricalcium phosphate and bioactive glass was 1:1.6. The tricalcium phosphate particles were prepared by above process having about 0.2~3 mm diameter and greater than or equal to about 70% porosity. The carrier was comprised by whole weight ratio of 12% glycerol, 10% PEG, 3% CMC and 10% water.

Elasticity and viscosity of the bone implant composition produced by this embodiment 4 was verified through the test method illustrated in the embodiment 1. Compressive modulus of the specimen of this embodiment 4 was 0.224 MPa, and it had a soft texture, could be easily shaped, and had excellent handleability during hand test by a controller.

Embodiment 5

All carriers were mixed in 70° C. water bath and then ceramic particles were added. Mixture comprised by weight ratio of 70% ceramic particles and 30% carriers was mixed and stirred for 10 minutes and then cooled to room temperature. Wherein, ceramic particles were comprised by whole weight ratio of 10% tricalcium phosphate and 60% bioactive glass. The weight ratio of tricalcium phosphate and bioactive glass was 1:6. The tricalcium phosphate particles were prepared by above process having about 0.2~3 mm diameter and greater than or equal to about 70% porosity. The carrier was comprised by whole weight ratio of 5% glycerol, 18% PEG, 5% CMC and 2% water.

Elasticity and viscosity of the bone implant composition produced by this embodiment 5 was verified through the test method illustrated in the embodiment 1. Compressive modulus of the specimen of this embodiment 5 was 0.346 MPa, and it had a soft texture, could be easily shaped, and had excellent handleability during hand test by a controller.

Animal Test

The bone implant composition was produced from embodiment 4 for a test sample of experimental group. A commercial product composing whole weight ratio of 69% bioactive glass, 19% glycerol and 12% PEG was brought as a test sample of control group.

10 New Zealand white rabbits in 6 months age and 3.5~4.5 kilogram weight were divided into two groups, treatment after 3 and 6 months, for 5 rabbits respectively, and each group was further divided into experimental group, control group and blank group. After anaesthetization of isoflurane gas to the subject rabbit, a hole of ∅ 6×8 millimeter (mm) was drilled at the femoral condyle. Samples of experimental and control group were filled into the defect of femoral condyles at both femurs. No sample was implanted into the defect for blank group. The incision was closed layer by layer after operation. Appearance, breathe, reflex and behavior of rabbits were observed every week, and nothing unusual was observed during research. Weight of these rabbits were measured every month. All rabbits gained weights slightly or had no significant changes compared to pre-operation condition. Rabbits were sacrificed under humanitarian principles after treatment for 3 or 6 months.

Femur samples were taken and preserved in 75% alcohol for fixation, then hematoxylin and eosin staining of these samples were proceeded.

Figure 3:
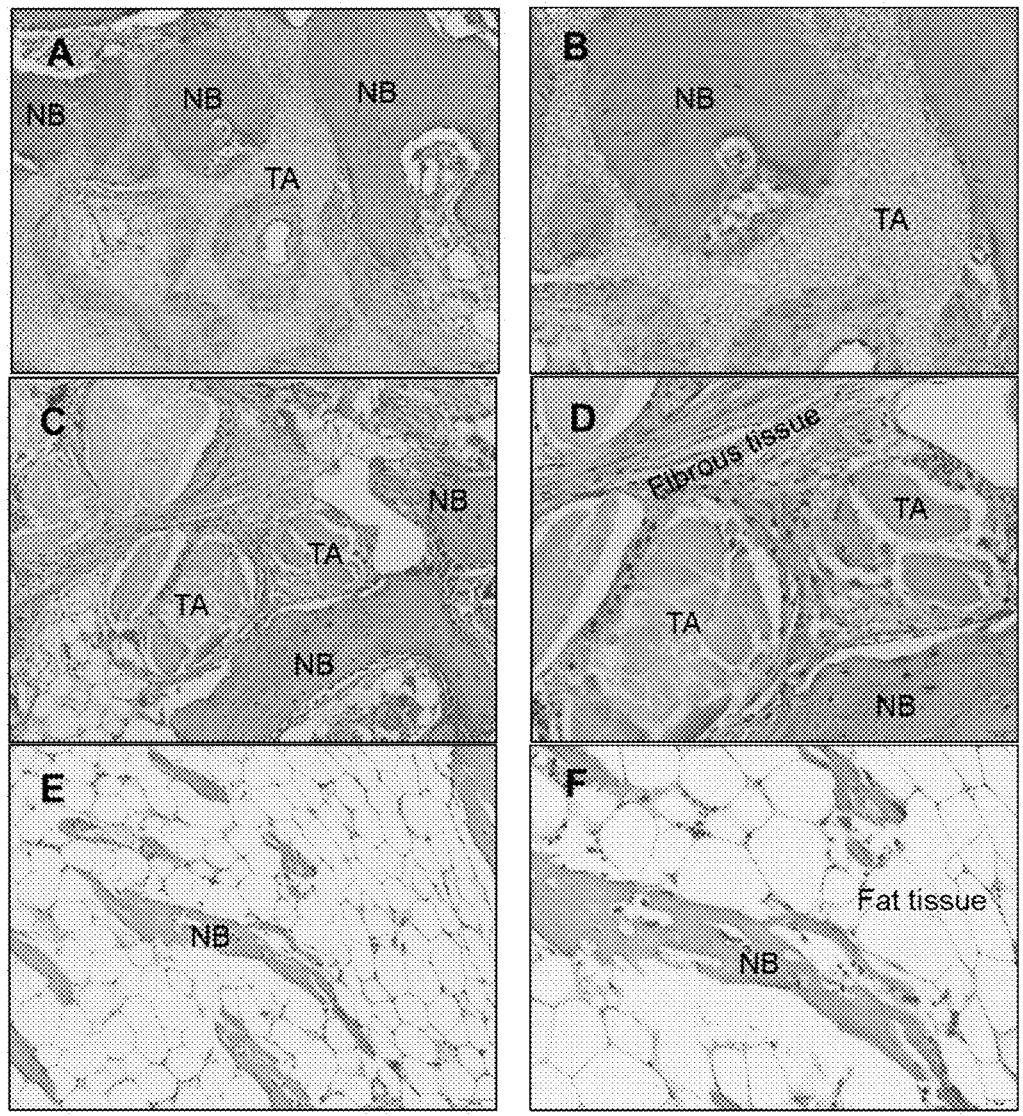
FIG. 3 is an image showing hematoxylin and eosin-stained tissues from results of animal test in the present invention. Each tissue is a part of implanted bone defect obtained from a subject which underwent surgery and was sacrificed after 3 months, wherein images A, B show tissues from subject of treatment group, images C, D show tissues from subject of control group, images E, F show tissues from subject of non-treatment group. The "NB" tags on images show new bone and the "TA" tags on images show residual implant.

Histomorphology images after treatment for 3 months are shown as FIG. 3. Compared with control group, new bones (NB) with increased sizes and obvious precipitation of experimental group can be observed in FIG. 3A and FIG. 3B, and residual materials adhered closely with new bones. The sample of experimental group shows good biocompatibility and can build good connections with bone tissues. The sample of control group in bone defect was degraded, and new bones and a slight fibrous tissues were formed (FIG. 3C and FIG. 3D), which means the sample of control group induced immune reaction after implantation and repaired by fibrous tissues. It further indicated that the affinity of the sample of control group and bone tissues was low. There were limited new bone growth and multilayer fat tissues infiltration in blank group (FIG. 3E and FIG. 3F).

Figure 4:
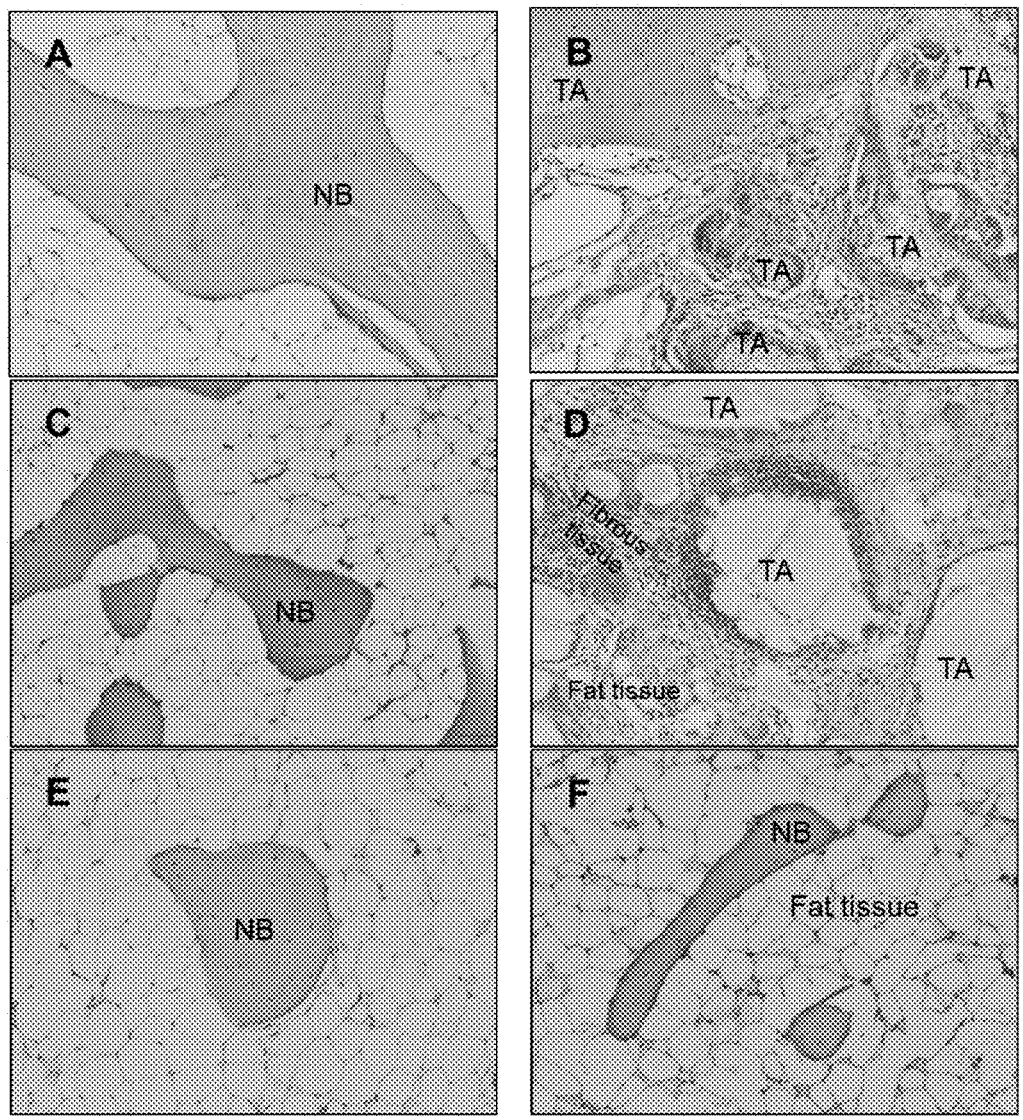
FIG. 4 is an image showing hematoxylin and eosin-stained tissues from results of animal test in the present invention. Each tissue is a part of implanted bone defect obtained from a subject which underwent surgery and was sacrificed after 6 months, wherein images A, B show tissues from subject of treatment group, images C, D show tissues from subject of control group, images E, F show tissues from subject of non-treatment group. The "NB" tags on images show new bone and the "TA" tags on images show residual implant.

Histomorphology images after treatment for 6 months are shown as FIG. 4. The sample of experimental group in bone defect was almost degraded, and thick and branched new lamellar bones grew, wherein FIG. 4B shows that the sample of experimental group was dissolved and new lamellar bones were formed. The sample of control group in bone defect was almost degraded, new lamellar bones and multilayer fat cells grew (FIG. 4C and FIG. 4D), wherein FIG. 4D shows that the sample of control group was dissolved and embedded by fibrous tissues. It indicated that the sample of control group was degraded faster than the sample of experimental group did, leading fat tissues, not new bone tissues, to fill the empty space. There were new lamellar bone fragments and lot of fat tissues infiltration in blank group (FIG. 4E and FIG. 4F).

According to above animal test, for new bone growth, each of experimental group and control group had significant new bone growth by comparing with a lot of histomorphology images from blank group after treatment for 6 months. Wherein, experimental group induced more new bone growth than control group and the experiment results show significant differences. For materials degradation, the sample of experimental group had more material residues than control group by comparing with a lot of histomorphology images after treatment for 6 months, which indicates that the sample of experimental group can constantly provide biological supports in the bone defect.

To sum up, according to embodiments, animal tests and detailed explanations thereof, the bone implant composition of this present invention has a high proportion of ceramic particles for total amount of 50~70% and comprises tricalcium phosphate and bioactive glass. The tricalcium phosphate can induce adhesion and growth of new bone cells, and the bioactive glass can induce growth factors and promote growth of new bone cells. Therefore, ceramic particles can still construct supports even if carrier was degraded within a short time after implanted, which is beneficial for adhesion and growth of new bone cells, and also promotes healing of bone defect. Furthermore, tricalcium phosphate for this present invention has high porosity and appropriate sizes which can help new bone cells attach and grow. Finally, the ingredient and proportion of carrier in this present invention maintain a good ability for operation of the bone implant composition with a high ratio of ceramic particles. Based on test procedure above, the bone implant composition of this present invention can be easily shaped, and has a soft texture and excellent handleability during hand test by a controller while compressive modulus of the bone implant composition is 0.110~0.512 MPa. It will benefit surgeons for operation and increase usability.

It should be pointed out that the embodiment detailed above with reference to the accompanying drawings serves only to expound the technical contents and features of the present invention. A person of ordinary skill in the art who understands the technical contents and features of the invention may make various simple modifications or substitutions or reduce the disclosed components without departing from the spirit of the invention. All such modifications, substitutions, and component reductions shall fall within the scope of the invention.

What is claimed is:
1. A bone implant composition, comprising:
   50-70% by weight of ceramic particles, wherein the ceramic particles comprising tricalcium phosphate and bioactive glass;
   30-50% by weight of carrier; and
   wherein the compressive modulus value of the bone implant composition is 0.110-0.512 MPa.
2. The bone implant composition of claim 1, wherein the tricalcium phosphate and the bioactive glass are present in a ratio by weight of 1:0.22 to 1:6.
3. The bone implant composition of claim 1, wherein the diameter of the tricalcium phosphate is 0.2-3 mm.
4. The bone implant composition of claim 1, wherein the porosity of the tricalcium phosphate is greater than or equal to 70%.
5. The bone implant composition of claim 1, wherein the carrier composes glycerol, polyethylene glycol and carboxymethyl cellulose.
6. The bone implant composition of claim 5, wherein the carrier further composes water.
7. The bone implant composition of claim 1, wherein all materials are present in a ratio by weight of 5-20% glycerol, 10-25% polyethylene glycol, 2-5% carboxymethyl cellulose and 0-10% water.

* * * * *